United States Patent
Li et al.

(10) Patent No.: US 8,889,108 B2
(45) Date of Patent: *Nov. 18, 2014

(54) COSMETIC COMPOSITIONS COMPRISING LATEX FILM FORMERS

(71) Applicant: L'Oreal S.A., Paris (FR)

(72) Inventors: Chunhua Li, Scotch Plains, NJ (US); Hy Si Bui, Piscataway, NY (US); Jean-Thierry Simonnet, Mamaroneck, NY (US); Anne Wagner, Philadelphia, PA (US); Ruth Josie Donat, Union, NJ (US)

(73) Assignee: L'Oreal, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 13/632,536

(22) Filed: Oct. 1, 2012

(65) Prior Publication Data

US 2013/0084255 A1    Apr. 4, 2013

Related U.S. Application Data

(60) Provisional application No. 61/542,136, filed on Sep. 30, 2011.

(51) Int. Cl.
*A61K 8/18* (2006.01)
*A61Q 3/02* (2006.01)
*A61K 8/81* (2006.01)
*A61Q 1/06* (2006.01)
*A61K 8/37* (2006.01)

(52) U.S. Cl.
CPC . *A61K 8/375* (2013.01); *A61Q 3/02* (2013.01); *A61K 8/8152* (2013.01); *A61Q 1/06* (2013.01)
USPC .......................................................... 424/61

(58) Field of Classification Search
None
See application file for complete search history.

(56) References Cited

U.S. PATENT DOCUMENTS

| | | | |
|---|---|---|---|
| 4,126,675 A | 11/1978 | Boulogne et al. | |
| 4,289,752 A | 9/1981 | Mahieu et al. | |
| 4,537,916 A * | 8/1985 | Bruschtein et al. | 523/201 |
| 5,370,866 A | 12/1994 | Frankfurt et al. | |
| 5,538,717 A | 7/1996 | La Poterie | |
| 5,693,716 A * | 12/1997 | Bott et al. | 525/291 |
| 6,238,651 B1 | 5/2001 | Bara | |
| 6,372,201 B1 | 4/2002 | Leuridan et al. | |
| 6,458,390 B1 * | 10/2002 | Manelski et al. | 424/617 |
| 7,025,953 B2 | 4/2006 | Blin et al. | |
| 2003/0026815 A1 * | 2/2003 | Scott et al. | 424/401 |

* cited by examiner

*Primary Examiner* — Anand Desai
*Assistant Examiner* — Melissa Mercier
(74) *Attorney, Agent, or Firm* — The Marbury Law Group, PLLC

(57) ABSTRACT

Disclosed are cosmetic compositions comprising at least one latex-film former chosen from at least one acrylate copolymer and derivatives thereof, and at least one coalescent and/or plasticizer.

16 Claims, No Drawings ical compositions comprising (1) at least one latex film former, and (2) at least one coalescent and/or plasticizer. Latex film formers useful in various embodiments of the disclosure may be chosen from acrylate copolymers and derivatives thereof. Cosmetic compositions according to various embodiments of the disclosure may have improved properties, such as improved water- and/or oil-resistance, shine, adhesion, hardness, and/or long wear.

COSMETIC COMPOSITIONS COMPRISING LATEX FILM FORMERS

FIELD OF THE DISCLOSURE

The disclosure relates to cosmetic compositions comprising (1) at least one latex film former, and (2) at least one coalescent and/or plasticizer. Latex film formers useful in various embodiments of the disclosure may be chosen from acrylate copolymers and derivatives thereof. Cosmetic compositions according to various embodiments of the disclosure may have improved properties, such as improved water- and/or oil-resistance, shine, adhesion, hardness, and/or long wear.

BACKGROUND

Film formers, coalescents, and plasticizers are well-known in the cosmetic field. Inclusion of a film former in a cosmetic composition can improve various properties, such as, for example, shine, adhesion, and long wear. It is also known that inclusion of a coalescent agent promotes the coalescence of polymer particles in an aqueous dispersion, and inclusion of a plasticizer makes it possible to plasticize a polymer in an aqueous dispersion.

The use of latex film formers in cosmetic compositions is also known, for example, in mascara, hair styling products, topical foundation, sunscreen compositions, and water-based nail enamel. In particular, latex and latex blends have been used to provide extended-wear properties of the cosmetic product into which they are formulated. For example, conventional washable mascara compositions use latex film formers in combination with an oil-in-water emulsion.

However, it has been found that cosmetic compositions having film formers may have less than satisfactory properties. For example, nail varnish compositions are known which comprise aqueous dispersions of particles of a film-forming polymer, wherein the film may exhibit poor adhesion to the nail and/or may not be sufficiently bright.

There is a desire in the cosmetic industry to provide consumers with products having improved properties such as improved shine, adhesion, and long wear. As such, there is a continuous need to invent novel cosmetic compositions which demonstrate one or more improved property.

It has now been surprisingly discovered that by incorporating (1) at least one latex film former, and (2) at least one coalescent and/or plasticizer into cosmetic compositions, cosmetic properties such as water- and/or oil-resistance, shine, adhesion, hardness, and/or long wear can be improved.

DESCRIPTION OF EXEMPLARY EMBODIMENTS

The disclosure relates, in various embodiments, to cosmetic compositions comprising (1) at least one latex film former, and (2) at least one coalescent.

Latex film formers useful according to the disclosure may be chosen from acrylate copolymers and derivatives thereof. According to various embodiments of the disclosure, the at least one acrylate copolymer and derivatives thereof may be chosen from those having a glass transition temperature (Tg) ranging from about 15° C. to about 100° C., such as from about 30° C. to about 70° C. By way of example only, an ammonium acrylates copolymer, an acrylates copolymer, and/or derivatives thereof may be chosen. Exemplary commercial acrylate copolymer products that may be used include, but are not limited to, DERMACRYL AQF by AkzoNobel; and SYNTRAN PC5620 and SYNTRAN KL219 by Interpolymer Corporation.

In various exemplary embodiments, the at least one latex film former may be present in the cosmetic composition in an amount ranging from about 10% to about 90%, such as about 20% to about 80%, about 25% to about 75%, or about 30% to about 60%. In at least one exemplary embodiment, the at least one latex film former is present in the cosmetic composition in an amount ranging from about 25% to about 35%, such as about 28% to about 30%.

As described herein, the cosmetic compositions comprising at least one latex film former further comprise at least one coalescent and/or plasticizer. Plasticizers useful according to various embodiments of the disclosure include one or more chosen from tributyl citrate, texanol ester alcohol, and diisobutyl adipate. Coalescents useful according to various embodiments of the disclosure include one or more chosen from propylene glycol n-butyl ether and dipropylene glycol benzoate. In various embodiments, the at least one coalescent and/or plasticizer may be added in a combined amount of up to about 10%, such as up to about 7%, or up to about 5%. In various exemplary embodiments, the at least one coalescent and/or plasticizer may be added in a combined amount ranging from about 1% to about 5%, such as about 1% to about 3%.

One embodiment of the disclosure relates to cosmetic compositions comprising (1) at least one latex film former chosen from an ammonium acrylates copolymer, and (2) at least one coalescent and/or plasticizer. In one exemplary embodiment, the latex film former may, by way of example, be an ammonium acrylates copolymer chosen from SYNTRAN KL219. In various exemplary embodiments, the at least one coalescent may be chosen from glycol n-butyl ether and dipropylene glycol dibenzoate. In various exemplary embodiments, the at least one plasticizer may be chosen from tributyl citrate, texanol ester alcohol, and diisobutyl adipate.

Another embodiment of the disclosure relates to cosmetic compositions comprising (1) at least one latex film former chosen from an acrylates copolymer, and (2) at least one coalescent and/or plasticizer. In one exemplary embodiment, the latex film former may, by way of example, be acrylates copolymer (and) butylene glycol (and) sodium laureth sulfate, such as, for example, SYNTRAN PC5620. In various exemplary embodiments, the at least one plasticizer may be chosen from texanol ester alcohol and diisobutyl adipate.

Another embodiment of the disclosure relates to cosmetic compositions comprising (1) at least one latex film former chosen from an ammonium acrylates copolymer, and (2) at least one coalescent and/or plasticizer. In one exemplary embodiment, the latex film former may, by way of example, be an ammonium acrylates copolymer chosen from DERMACRYL AQF. In various exemplary embodiments, the at least one coalescent may be chosen from dipropylene glycol dibenzoate. In various exemplary embodiments, the at least one plasticizer may be chosen from tributyl citrate, texanol ester alcohol, and diisobutyl adipate.

In addition, other cosmetic ingredients may be included in the compositions according to the disclosure. Such ingredients are known, and include but are not limited to solvents (including water), colorants, humectants, emulsifiers, surfactants, preservatives, fragrances, thickeners or texturizers, emollients, plasticizers, and additional film-formers and/or coalescents. One of skill in the art will be able to select appropriate types and amounts of additional cosmetic ingredients, based on, for example, the type of cosmetic composition being formulated and the desired properties thereof. By way of example only, such additional cosmetic ingredients may be present in the compositions according to the disclosure in a combined amount ranging from about 10% to about 80%, such as about 15% to about 60%, about 25% to about 40%, or about 30% to about 35%.

Exemplary cosmetic compositions contemplated according to the disclosure include compositions intended for application to keratinous fibers, such as the hair, skin, and nails. Such compositions include, but are not limited to, nail compositions (e.g. nail enamel), mascara compositions, make-up compositions (e.g. foundations), sunscreen compositions, and hair-care compositions (e.g. hair-styling compositions).

Without wishing to be bound by theory, it is believed that the combination of the at least one latex film former described herein and at least one coalescent and/or plasticizer surprisingly and unexpectedly shows a synergistic effect, imparting improved properties such as, for example, improved water- and/or oil-resistance, shine, adhesion, hardness, and/or long-wear to the cosmetic compositions. By way of example only, mascara formulations comprising at least one latex film former described herein and at least one coalescent and/or plasticizer have been found to have improved curl, curl-retention, volume, and long-wear properties, which are seen for several days after application. As a further non-limiting example, nail formulations, such as water-based nail enamel formulations, comprising a latex film former comprising at least one latex film former described herein, and at least one coalescent and/or plasticizer, have been found to have improved shine, smoothness on application, hardness, and long-wear properties. It should be noted, however, that compositions according to the disclosure may not have one or more of the above-referenced improved properties, yet such compositions are intended to be within the scope of the disclosure.

It is to be understood that both the foregoing description and the following Example are exemplary and explanatory only, and are not to be interpreted as restrictive of the disclosure. Moreover, it should be understood that various features and/or characteristics of differing embodiments herein may be combined with one another. It is therefore to be understood that numerous modifications may be made to the illustrative embodiments and that other arrangements may be devised without departing from the scope of the invention. Other embodiments will be apparent to those skilled in the art from consideration of the disclosure and practice of the various exemplary embodiments disclosed herein.

It is also to be understood that, as used herein the terms "the," "a," or "an," mean "at least one," and should not be limited to "only one" unless explicitly indicated to the contrary. Thus, for example, the use of "a plasticizer" is intended to mean at least one plasticizer.

Unless otherwise indicated, all numbers used in the specification and claims are to be understood as being modified in all instances by the term "about," whether or not so stated. It should also be understood that the precise numerical values used in the specification and claims form additional embodiments of the invention, and are intended to include any ranges which can be narrowed to any two end points disclosed within the exemplary ranges and values provided. Efforts have been made to ensure the accuracy of the numerical values disclosed herein. Any measured numerical value, however, can inherently contain certain errors resulting from the standard deviation found in its respective measuring technique.

EXAMPLES

The following Examples are intended to be non-restrictive and explanatory only, with the scope of the invention being defined by the claims.

Examples 1 and 2

Simple Mascara Compositions

Two simple mascara compositions were made by mixing, independently, the components set forth in the following Table 1 and Table 2.

TABLE 1

| Trade Name | INCI Name | Weight % |
|---|---|---|
| DERMACRYL AQF | ammonium acrylates copolymer | 43.75 |
| JONCRYL77 | styrene/acrylates copolymer | 43.75 |
| SCANDINOL SP 21 | Tributyl Citrate | 2.2 |
| Distinctive Ink Black PV AQII | Black 2 | 5 |
| Expert Gel EG56 | Bis-Methoxy PEG-13 PEG-438/ PPG-110 SMDI Copolymer | 1 |
| QS Water | QS Water | 4.3 |
| TOTAL | | 100% |

TABLE 2

| Trade Name | INCI Name | Weight % |
|---|---|---|
| DERMACRYL AQF | ammonium acrylates copolymer | 43.75 |
| JONCRYL77 | styrene/acrylates copolymer | 43.75 |
| SCANDINOL SP 21 | Tributyl Citrate | 1.5 |
| | Dipropylene Glycol Dibenzoate | 1.5 |
| QS Water | QS Water | 9.5 |
| TOTAL | | 100% |

Example 3

Mascara Composition

Two batches of a mascara composition were prepared having the composition shown in Table 3, by following the procedure set forth in Table 4.

TABLE 3

| Phase | INCI Name | Trade Name | Conc. | Weight (g) | Weight (g) |
|---|---|---|---|---|---|
| A1 | DI Water | DI Water | 29.43 | 294.30 | 147.15 |
| A1 | Methylparaben | Methyl Paraben | 0.33 | 3.30 | 1.65 |
| A1 | Phenoxyethanol | Phenoxyethanol | 0.84 | 8.40 | 4.20 |
| A1 | Ethylparaben | Ethyl Paraben | 0.22 | 2.20 | 1.10 |
| A1 | Disodium EDTA | Disodium EDTA | 0.20 | 2.00 | 1.00 |
| A1 | Sodium Dehydroacetate | Sodium Dehydroacetate | 0.20 | 2.00 | 1.00 |
| A1 | Butylene Glycol | Butylene Glycol | 2.40 | 24.00 | 12.00 |
| A1 | Simethicone | Simethicone | 0.10 | 1.00 | 0.50 |

TABLE 3-continued

| Phase | INCI Name | Trade Name | Conc. | Weight (g) | Weight (g) |
|---|---|---|---|---|---|
| A1 | PEG-200 Glyceryl Stearate | SIMULSOL 220 | 3.00 | 30.00 | 15.00 |
| A2 | Black Iron Oxide | Sunpuro Black | 7.000 | 70.00 | 35.00 |
| A3 | ACRYLAMIDE/SODIUM ACRYLOYLDIMETHYL-TAURATE COPOLYMER | SIMULGEL 600 | 2.00 | 20.00 | 10.00 |
| B1 | Beeswax | White Beeswax SP 453P | 7.18 | 71.80 | 35.90 |
| B1 | Carnauba Wax | Carnauba Wax SP63 | 4.00 | 40.00 | 20.00 |
| B1 | Cetyl Alcohol | Acilol 16 | 2.00 | 20.00 | 10.00 |
| B1 | VP/EICOSENE COPOLYMER | Antaton V220 | 2.00 | 20.00 | 10.00 |
| B1 | Glyceryl Stearate | Glyceryl Stearate | 1.00 | 10.00 | 5.00 |
| B1 | ETHYLENEDIAMINE/STEARYL DIMER DILINOLEATE COPOLYMER | UNICLEAR 100VG | 2.00 | 20.00 | 10.00 |
| B1 | *SIMMONDSIA CHINENSIS* (JOJOBA) BUTTER | ISO JOJOBA 50 | 2.00 | 20.00 | 10.00 |
| C | Joncryl 77/Dermacryl AQF/1.5% Tributyl Citrate | | 30.00 | 300.00 | 150.00 |
| D | Caprylyl Glycol | Caprylyl Glycol | 1.00 | 10.00 | 5.00 |
| D | Denatured Alcohol | Denatured Alcohol | 3.00 | 30.00 | 15.00 |
| D | Soluble Collagen | Soluble Collagen | 0.10 | 1.00 | 0.50 |
| TOTAL | | | 100.00 | 1000.00 | 500.00 |

TABLE 4

| Operation | Scraper RPM | Agitator RPM | Homo RPM | VAC Bar | TEMP °C. |
|---|---|---|---|---|---|
| Charge Phase A1 and Phase A2 to Main Kettle (MK) and mix for 60 minutes to properly disperse pigments. Begin heating to 55° C. | 0 | 0 | 800 | — | RT/55 |
| Charge Phase A3 to MK and mix for 5 minutes. Batch will become thicker as A3 becomes incorporated. Continue heating to 95° C. | 0 | 0 | 1100 | — | 55/95 |
| Melt Phase B1 in Side Kettle (SK) on Hot Plate. Heat to 95° C. and verify all waxes are melted. | | | Hot Plate | | |
| Charge SK to MK and emulsify for 20 minutes. Maintain temperature at 95° C. | 0 | 0 | 1500 | — | 95 |
| Start cooling batch to 45° C. with sweep mixing only. | Min | — | — | — | 95/45 |
| At 45° C., add Phase C one component at a time. Mix until dispersed and uniform. Increase mixer speed if needed to properly incorporate large amount of film formers added at this stage. | Min | — | — | — | 45 |
| Continue cooling to 30° C. with sweep mixing. | Min | — | — | — | 45/30 |
| At 30° C., charge Phase D to MK and mix until uniform. | Min | — | — | — | 30 |

The mascara compositions prepared in Tables 1 and 3 above were tested on eyelashes. The resulting products demonstrated improved properties of thickness, curl, volume, and long wear. These properties were still visible after two days.

Example 4

Water-based Nail Enamel

A water-based nail enamel was prepared having the following composition, as shown in Table 5:

TABLE 5

| INCI Name | Trade Name | Weight % (Raw Material) | Weight % (Active) |
|---|---|---|---|
| Water | Water | 8.11 | qs |
| Styrene acrylic emulsion | RHOPLEX P376 | 20 | 10 |
| Acrylic copolymer | DERMACRYL AQF | 55.55 | 25 |
| Propylene glycol n-butyl ether | DOWANOL PNB | 2.1 | 2 |
| Dipropylene glycol dibenzoate | | 2 | 2 |
| Pigment dispersion | | 12.24 | 3 |
| TOTAL | | 100 | 100 |

The nail enamel composition was tested and found to have improved properties of shine, smoothness upon application, water- and oil-resistance, hardness, and long wear. These properties were seen to last for several days.

What is claimed is:

1. A nail cosmetic composition comprising:
   a. at least one latex film former chosen from ammonium acrylates copolymers, acrylates copolymers, and derivatives thereof, having a Tg ranging from about 30° C. to about 70° C., and present in an amount ranging from about 20% to about 80% by weight;
   b. at least one coalescent chosen from glycol n-butyl ether and dipropylene glycol dibenzoate; and
   c. at least one plasticizer chosen from tributyl citrate, texanol ester alcohol, and diisobutyl adipate;
   wherein the at least one coalescent and the at least one plasticizer are present in a combined amount of less than or equal to about 10% by weight.

2. The nail cosmetic composition of claim 1, wherein the at least one latex film former is chosen from ammonium acrylates copolymers having a Tg ranging from about 30° C. to about 70° C. and derivatives thereof.

3. The nail cosmetic composition of claim 1, wherein the at least one latex film former is present in the nail cosmetic composition in an amount ranging from about 35% to about 80% by weight.

4. The nail cosmetic composition of claim 1, wherein the at least one coalescent is dipropylene glycol dibenzoate.

5. The nail cosmetic composition of claim 1, wherein the at least one plasticizer is tributyl citrate.

6. The nail cosmetic composition of claim 1, wherein the at least one coalescent and the at least one plasticizer are present in a combined amount of less than or equal to about 5% by weight.

7. The nail cosmetic composition of claim 1, wherein the composition is a nail polish.

8. A nail polish composition comprising:
   a. at least one latex film former chosen from ammonium acrylates copolymers having a Tg ranging from about 30° C. to about 70° C. and derivatives thereof, present in an amount ranging from about 60% to about 80% by weight;
   b. at least one coalescent chosen from glycol n-butyl ether and dipropylene glycol dibenzoate; and
   c. at least one plasticizer chosen from tributyl citrate, texanol ester alcohol, and diisobutyl adipate;
   wherein the at least one coalescent and the at least one plasticizer are present in a combined amount of less than or equal to about 5% by weight.

9. The nail polish composition of claim 8, wherein the at least one coalescent is dipropylene glycol dibenzoate and the at least one plasticizer is tributyl citrate.

10. A method of improving at least one property chosen from adhesion, water-resistance, oil-resistance, shine, and long-wear properties in a nail cosmetic composition, said method comprising including in the nail cosmetic composition:
    a. from about 20% to about 80% by weight of at least one latex film former chosen from ammonium acrylates copolymers, acrylates copolymers, and derivatives thereof, having a Tg ranging from about 30° C. to about 70° C.;
    b. at least one coalescent chosen from glycol n-butyl ether and dipropylene glycol dibenzoate; and
    c. at least one plasticizer chosen from tributyl citrate, texanol ester alcohol, and diisobutyl adipate;
    wherein the at least one coalescent and the at least one plasticizer are present in a combined amount of less than or equal to about 10% by weight.

11. The method of claim 10, wherein the at least one latex film former is chosen from ammonium acrylates copolymers having a Tg ranging from about 30° C. to about 70° C.

12. The method of claim 10, wherein the at least one latex film former is present in the nail cosmetic composition in an amount ranging from about 35% to about 80% by weight.

13. The method of claim 10, wherein the at least one coalescent is dipropylene glycol dibenzoate.

14. The method of claim 10, wherein the at least one plasticizer is tributyl citrate.

15. The method of claim 10, wherein the at least one coalescent and the at least one plasticizer are present in a combined amount of less than or equal to about 5% by weight.

16. The method of claim 10, wherein the nail cosmetic composition is a nail polish.

* * * * *

UNITED STATES PATENT AND TRADEMARK OFFICE
CERTIFICATE OF CORRECTION

PATENT NO. : 8,889,108 B2  
APPLICATION NO. : 13/632536  
DATED : November 18, 2014  
INVENTOR(S) : Chunhua Li et al.

Page 1 of 1

It is certified that error appears in the above-identified patent and that said Letters Patent is hereby corrected as shown below:

On the Title Page, Item (71), change "L'Oreal S.A." to --L'OREAL--.

Signed and Sealed this
Tenth Day of March, 2015

Michelle K. Lee
*Deputy Director of the United States Patent and Trademark Office*